(12) United States Patent
Sato et al.

(10) Patent No.: US 10,578,553 B2
(45) Date of Patent: Mar. 3, 2020

(54) MEASURING APPARATUS

(71) Applicants: PIONEER CORPORATION, Bunkyo-ku, Tokyo (JP); NIKKISO COMPANY LIMITED, Tokyo (JP)

(72) Inventors: Mitsuru Sato, Kawagoe (JP); Kiyoshi Tateishi, Kawagoe (JP); Wataru Onodera, Kawagoe (JP); Atsuya Ito, Kawagoe (JP); Tomoya Murakami, Makinohara (JP); Akari Agata, Makinohara (JP); Genki Adachi, Makinohara (JP)

(73) Assignees: PIONEER CORPORATION, Tokyo (JP); NIKKISO COMPANY LIMITED, Tokyo (JP)

( * ) Notice: Subject to any disclaimer, the term of this patent is extended or adjusted under 35 U.S.C. 154(b) by 0 days.

(21) Appl. No.: 16/464,836

(22) PCT Filed: Nov. 29, 2016

(86) PCT No.: PCT/JP2016/085299
§ 371 (c)(1),
(2) Date: May 29, 2019

(87) PCT Pub. No.: WO2018/100603
PCT Pub. Date: Jun. 7, 2018

(65) Prior Publication Data
US 2019/0293557 A1   Sep. 26, 2019

(51) Int. Cl.
*G01N 21/53*   (2006.01)
*A61B 5/0285*  (2006.01)
(Continued)

(52) U.S. Cl.
CPC .......... *G01N 21/53* (2013.01); *A61B 5/0285* (2013.01); *G01P 5/26* (2013.01); *G01N 2015/0065* (2013.01)

(58) Field of Classification Search
CPC ....... G01N 2011/08; G01N 2015/0065; G01N 2015/0693; G01N 15/06; G01N 21/47;
(Continued)

(56) References Cited

U.S. PATENT DOCUMENTS 3,762,221 A * 10/1973 Coulthard ............ A61B 5/0261
                                                      73/861.06
4,596,254 A *  6/1986 Adrian ................. A61B 5/0261
                                                      356/28
(Continued)

FOREIGN PATENT DOCUMENTS

EP   2837327 A1   2/2015
JP   H02-206430 A  8/1990
(Continued)

OTHER PUBLICATIONS

International Search Report, dated Jan. 10, 2017, from corresponding PCT application No. PCT/JP2016/085299.

*Primary Examiner* — Gordon J Stock, Jr.
(74) *Attorney, Agent, or Firm* — Young & Thompson

(57) ABSTRACT

These measurement devices are each provided with: irradiation unit that irradiate a fluid with light; a light-receiving unit that receives light scattered by the fluid; an acquiring unit that acquires fluid information which indicates the flow rate or the flow velocity of the fluid; and a control unit that controls the irradiation unit on the basis of the fluid information.

8 Claims, 4 Drawing Sheets

(51) Int. Cl.
*G01P 5/26* (2006.01)
*G01N 15/00* (2006.01)

(58) Field of Classification Search
CPC .......... G01N 21/4738; G01N 21/4788; G01N 21/49; G01N 21/53; G01N 2021/4769; G01N 2021/479; G01F 1/00; G01F 3/00; G01F 11/00; G01F 13/00; G01F 17/00; A61B 5/026; A61B 5/0261; A61B 5/0285; A61B 5/029; A61B 5/0295; G01P 5/001; G01P 5/26; A61M 1/36; A61M 1/3621; A61M 1/3663
See application file for complete search history.

(56) References Cited

U.S. PATENT DOCUMENTS

| | | | | |
|---|---|---|---|---|
| 4,988,190 A | * | 1/1991 | Miles | G01P 5/001 |
| | | | | 356/28 |
| 5,737,439 A | * | 4/1998 | Lapsley | A61B 5/1171 |
| | | | | 382/115 |
| 6,731,967 B1 | * | 5/2004 | Turcott | A61B 5/0261 |
| | | | | 600/407 |
| 7,420,658 B2 | | 9/2008 | Pettersson et al. | |
| 9,839,365 B1 | * | 12/2017 | Homyk | A61B 5/489 |
| 10,178,959 B1 | * | 1/2019 | Homyk | A61B 5/0261 |
| 2005/0243303 A1 | | 11/2005 | Pettersson et al. | |
| 2008/0275320 A1 | | 11/2008 | Pettersson et al. | |
| 2010/0056887 A1 | * | 3/2010 | Kimura | A61B 5/02028 |
| | | | | 600/324 |
| 2010/0069727 A1 | * | 3/2010 | Kawano | A61B 5/0261 |
| | | | | 600/310 |
| 2010/0069766 A1 | * | 3/2010 | Kawano | A61B 5/0261 |
| | | | | 600/504 |
| 2011/0190641 A1 | * | 8/2011 | Tateishi | A61B 5/0261 |
| | | | | 600/479 |
| 2013/0090564 A1 | * | 4/2013 | Tateishi | A61B 5/0261 |
| | | | | 600/479 |
| 2015/0080673 A1 | * | 3/2015 | Hashimoto | A61B 5/021 |
| | | | | 600/301 |
| 2015/0327782 A1 | * | 11/2015 | Tateishi | A61B 5/0261 |
| | | | | 600/479 |
| 2016/0198961 A1 | * | 7/2016 | Homyk | A61B 5/0082 |
| | | | | 600/476 |
| 2016/0338592 A1 | * | 11/2016 | Masumura | G01N 21/4795 |
| 2017/0319084 A1 | * | 11/2017 | Fujiwara | A61B 5/02007 |
| 2018/0014731 A1 | * | 1/2018 | Otsuka | A61B 5/0082 |
| 2018/0014735 A1 | * | 1/2018 | Otsuka | A61B 5/0082 |
| 2018/0049647 A1 | * | 2/2018 | Shi | A61B 5/0261 |
| 2018/0344176 A1 | * | 12/2018 | Nakashima | A61B 5/0261 |
| 2019/0059797 A1 | * | 2/2019 | Otsuka | A61B 5/14552 |
| 2019/0242814 A1 | * | 8/2019 | Bachalo | F02D 41/22 |

FOREIGN PATENT DOCUMENTS

| | | |
|---|---|---|
| WO | 2004/057313 A1 | 7/2004 |
| WO | 2013/153664 A1 | 10/2013 |

\* cited by examiner

MEASURING APPARATUS

TECHNICAL FIELD

The present invention relates to a measuring apparatus for and a measuring method of performing measurement on the basis of a signal obtained by applying light to a fluid, which flows inside a measurement target, and by receiving the light from the fluid, as well as a computer program, and a recording medium on which the computer program is recorded.

BACKGROUND ART

For this type of apparatus, for example, there is proposed an apparatus in which a light emitting diode (LED) and a light receiving element are arranged around a medical tubing and in which hematocrit of a blood that flows in the medical tubing is measured from a light receiving signal (refer to Patent Literature 1). Alternatively, there is proposed an apparatus configured to apply laser light to a tubing in which a blood flows, and configured to correct a blood flow volume, which is calculated from a Doppler shift of the laser light, on the basis of a blood concentration calculated from an amount of light received by the light receiving element (refer to Patent Literature 2).

CITATION LIST

Patent Literature

Patent Literature 1: WO 2004/057313 A1
Patent Literature 2: WO 2013/153664 A1

SUMMARY OF INVENTION

Technical Problem

If a fluid has a relatively high flow velocity, a laser light power may be increased in some cases to improve a signal to noise (SN) ratio. If the laser light power remains relatively high when the flow velocity of the fluid decreases for some reasons during the measurement, relatively high energy is applied to a part of the fluid by the irradiation of the laser light, which is technically problematic. This problem is not considered in the Patent Literatures 1 and 2.

It is therefore an object of the present invention to provide a measuring apparatus and a measuring method that can appropriately perform measurement even if the flow velocity of the fluid changes during the measurement, as well as a computer program and a recording medium.

Solution to Problem

The above object of the present invention can be achieved by a measuring apparatus provided with: a first irradiating device configured to apply light to a fluid; a first light receiving device configured to receive light scattered by the fluid, out of the light applied by the first irradiating device, and configured to output a first output signal; an obtaining device configured to obtain fluid information, which indicates a flow volume or a flow velocity of the fluid, on the basis of the first output signal of the first light receiving device; and a controlling device configured to control the first irradiating device, on the basis of the fluid information.

The above object of the present invention can be achieved by a measuring method in a measuring apparatus including: a first irradiating device configured to apply light to a fluid; and a first light receiving device configured to receive light scattered by the fluid, out of the light applied by the first irradiating device, and configured to output a first output signal, the measuring method provided with: an obtaining process of obtaining fluid information, which indicates a flow volume or a flow velocity of the fluid, on the basis of the first output signal of the first light receiving device; and a controlling process of controlling the first irradiating device, on the basis of the fluid information.

The above object of the present invention can be achieved by a computer program for making a computer, which is provided in a measuring apparatus including: a first irradiating device configured to apply light to a fluid; and a first light receiving device configured to receive light scattered by the fluid, out of the light applied by the first irradiating device, and configured to output a first output signal, function as: an obtaining device configured to obtain fluid information, which indicates a flow volume or a flow velocity of the fluid, on the basis of the first output signal of the first light receiving device; and a controlling device configured to control the first irradiating device, on the basis of the fluid information.

The above object of the present invention can be achieved by a recording medium on which the computer program of the present invention is recorded.

The effect of the present invention and other benefits will become apparent from the following description of embodiments.

DESCRIPTION OF EMBODIMENTS

Figure 1:
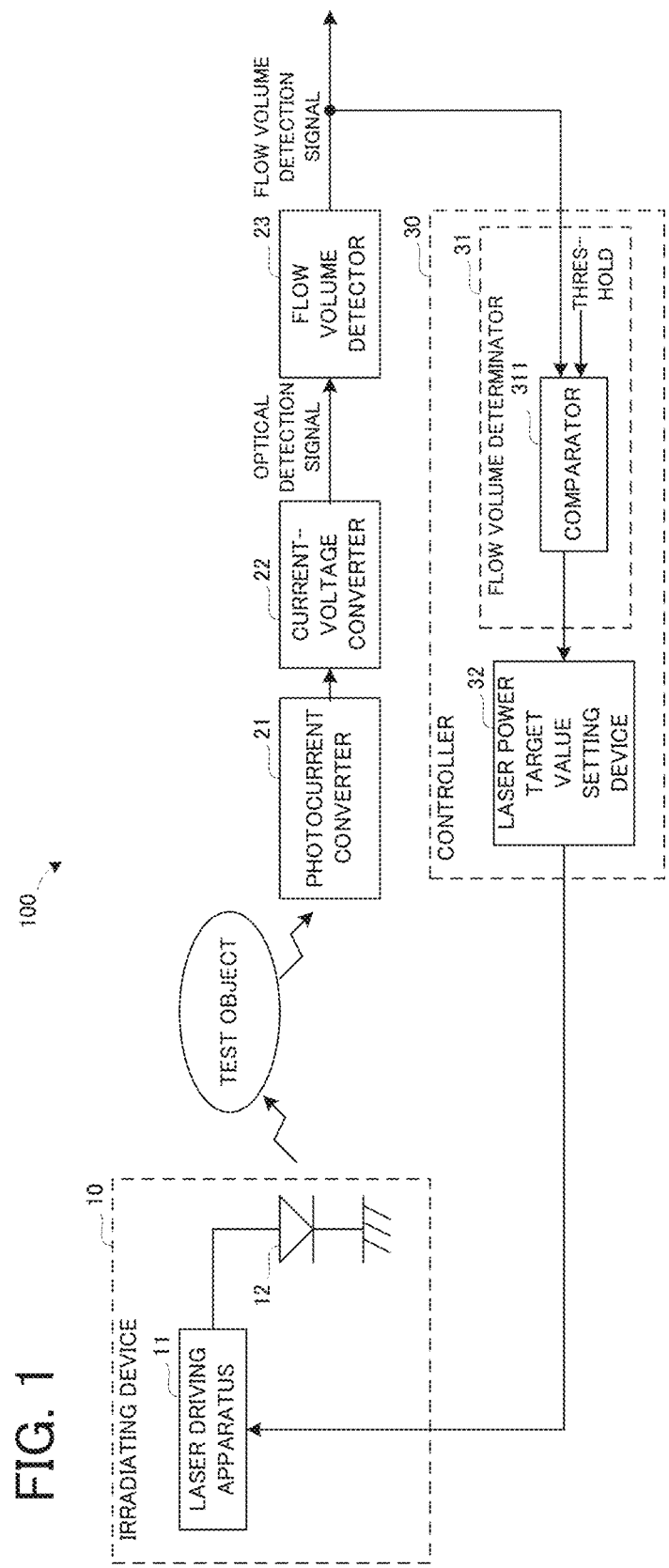
FIG. 1 is a block diagram illustrating a configuration of a laser Doppler blood-flowmetry according to a first practical example.

An explanation will be given to a measuring apparatus, a measuring method, a computer program, and a recording medium in embodiments of the present invention.

(Measuring Apparatus)

A measuring apparatus according to an embodiment is provided with: a first irradiating device configured to apply light to a fluid; a first light receiving device configured to receive light scattered by the fluid, out of the light applied by the first irradiating device, and configured to output a first output signal; an obtaining device configured to obtain fluid information, which indicates a flow volume or a flow velocity of the fluid, on the basis of the first output signal of the first light receiving device; and a controlling device configured to control the first irradiating device, on the basis of the fluid information.

According to the measuring apparatus in the embodiment, the first irradiating device is controlled on the basis of the fluid information, which indicates the flow volume of the flow velocity of the fluid. It is thus possible to appropriately perform measurement even if the flow velocity of the fluid changes during the measurement.

In an aspect of the measuring apparatus according to the embodiment, the controlling device is configured to control the first irradiating device to reduce intensity of the light applied to the fluid, or to stop irradiation of the light applied to the fluid, if the flow volume or the flow velocity of the fluid indicated by the fluid information is less than or equal to a first predetermined value. According to this aspect, it is possible to relatively easily determine whether to reduce the intensity of the light, or whether to stop the irradiation of the light. "To reduce the intensity of the light" may include that the intensity of the light is set to be zero.

The "first predetermined value" may be a value for determining whether or not to reduce the intensity of the light applied to the fluid, or whether or not to stop the irradiation of the light applied to the fluid, and may be set in advance as a fixed value, or a variable value corresponding to some physical quantity or parameter. Such a first predetermined value may be set as follows. For example, a relation between energy, which is applied per unit time to a portion of the fluid that is irradiated with the light, and the flow volume or the flow velocity may be obtained. Then, on the basis of the obtained relation, the first predetermined value may be set as the flow volume or the flow velocity at which the energy applied per unit time is an upper limit of an allowable range. The first predetermined value is typically set for each type of the fluid.

In this aspect, the first irradiating device may have a dimming device configured to reduce the light applied to the fluid, and the controlling device may be configured to control the first irradiating device to reduce the intensity of the light applied to the fluid by using the dimming device, if the flow velocity of the fluid indicated by the fluid information is less than or equal to the first predetermined value. By virtue of such a configuration, it is possible to relatively easily reduce the intensity of the light applied to the fluid. A specific example of the dimming device is, for example, a liquid crystal element, a mechanical shutter, or the like.

In this aspect, the measuring apparatus further comprises: a second irradiating device configured to apply light to the fluid; and a second light receiving device configured to receive light scattered by the fluid, out of the light applied by the second irradiating device, and configured to output a second output signal. The controlling device may be configured to control the first irradiating device to reduce the intensity of the light applied to the fluid from the first irradiating device, or to stop irradiation of the light applied to the fluid, while controlling the second irradiating device to maintain intensity of the light applied to the fluid from the second irradiating device, if the flow volume or the flow velocity of the fluid indicated by the fluid information is less than or equal to the first predetermined value. The intensity of the light applied to the fluid from the second irradiating device is weaker than the intensity of the light applied to the fluid from the first irradiating device.

In another aspect of the measuring apparatus according to the embodiment, the first output signal includes a beat signal caused by a Doppler shift of the light, and the obtaining device is configured: to obtain the fluid information on the basis of average frequency information and first-order moment information based on the beat signal; to obtain the fluid information on the basis of the average frequency information if the flow volume or the flow velocity of the fluid indicated by the fluid information is greater than or equal to a second predetermined value; and to obtain the fluid information on the basis of the first-order moment information if the flow volume or the flow velocity of the fluid indicated by the fluid information is less than the second predetermined value. According to this aspect, it is possible to improve the accuracy of the flow volume or the flow velocity indicated by the fluid information.

(Measuring Method)

A measuring method according to an embodiment is a measuring method in a measuring apparatus including: a first irradiating device configured to apply light to a fluid; and a first light receiving device configured to receive light scattered by the fluid, out of the light applied by the first irradiating device, and configured to output a first output signal, the measuring method provided with: an obtaining process of obtaining fluid information, which indicates a flow volume or a flow velocity of the fluid, on the basis of the first output signal of the first light receiving device; and a controlling process of controlling the first irradiating device, on the basis of the fluid information.

According to the measuring method in the embodiment, as in the measuring apparatus according to the embodiment described above, it is possible to appropriately perform measurement even if the flow velocity of the fluid changes during the measurement. The measuring method according to the embodiment can also adopt the same various aspects as those of the measuring apparatus according to the embodiment described above.

(Computer Program)

A computer program according to an embodiment makes a computer, which is provided in a measuring apparatus including: a first irradiating device configured to apply light to a fluid; and a first light receiving device configured to receive light scattered by the fluid, out of the light applied by the first irradiating device, and configured to output a first output signal, function as: an obtaining device configured to obtain fluid information, which indicates a flow volume or a flow velocity of the fluid, on the basis of the first output signal of the first light receiving device; and a controlling device configured to control the first irradiating device, on the basis of the fluid information.

According to the computer program in the embodiment, the measuring apparatus according to the embodiment described above can be relatively easily realized by making a computer, which is provided in the measuring apparatus, perform the computer program. As a result, according to the computer program in the embodiment, as in the measuring apparatus according to the embodiment described above, it is possible to appropriately perform measurement even if the flow velocity of the fluid changes during the measurement.

(Recording Medium)

On a recording medium according to an embodiment, the computer program according to the embodiment described above is recorded. The measuring apparatus according to the embodiment described above can be relatively easily realized as the computer provided in the measuring apparatus reads and executes the computer program recorded on a compact disc read only memory (CD-ROM), a DVD read only memory (DVD-ROM), or the like, which is an example of the recording medium according to the embodiment. As a result, according to the recording medium in the embodiment, as in the measuring apparatus according to the embodiment described above, it is possible to appropriately perform measurement even if the flow velocity of the fluid changes during the measurement.

Practical Examples

A measuring apparatus according to practical examples of the present invention will be explained with reference to the drawings. In the practical examples below, an example of the measuring apparatus of the present invention is a laser Doppler blood-flowmetry. An example of the fluid of the present invention is a blood.

First Practical Example

A laser Doppler blood-flowmetry according to a first practical example will be explained with reference to FIG. 1 and FIG. 2.

(Configuration)

A configuration of the laser Doppler blood-flowmetry according to the first practical example will be explained with reference to FIG. 1. FIG. 1 is a block diagram illustrating the configuration of the laser Doppler blood-flowmetry according to the first practical example.

In FIG. 1, a laser Doppler blood-flowmetry 100 is provided with an irradiating device 10, a photocurrent converter 21, a current-voltage converter 22, a flow volume detector 23, and a controller 30. The irradiating device 10, which is a specific example of the "first irradiating device" according to the present invention, is provided with a laser driving apparatus 11 and a light source 12, which is, for example, a laser diode. The controller 30 is provided with a flow volume determinator 31, and a laser power target value setting device 32 configured to set a target value associated with the laser driving apparatus 11.

Laser light emitted from the light source 12 of the irradiating device 10 is applied to a test object, which is a living body, such as, for example, a human. The laser light applied to the test object is scattered by biological tissues of the test object. The photocurrent converter 21, which is, for example, a photo diode, is configured to receive reflected light including backscattered light, out of the scattered laser light, and to output a current signal corresponding to a light amount of the received reflected light. The current-voltage converter 22 is configured to convert the current signal outputted from the photocurrent converter 21, to a voltage signal, and to output it as an optical detection signal.

The flow volume detector 23 is configured to output a flow volume detection signal associated with fluid information that indicates a flow volume of a blood of the test object, on the basis of the optical detection signal. A detailed explanation regarding how to obtain the flow volume on the basis of the optical detection signal will be omitted because the various existing methods can be applied, such as a method of obtaining the flow volume from an average frequency and a first-order moment, which are obtained, for example, by performing frequency analysis, such as fast Fourier transform, on the optical detection signal.

A comparator 311 of the flow volume determinator 31 is configured to compare the flow volume indicated by the fluid information with a threshold value, which is a specific example of the "first predetermined value" according to the present invention, and to output a comparison result. Here, the threshold value may be a fixed value or a variable value. The laser power target value setting device 32 is configured to set a target value associated with the laser driving apparatus 11 in accordance with the comparison result from the comparator 311.

Specifically, if the comparison result is that the flow volume is greater than the threshold value, the laser power target value setting device 32 may set, as the target value, a value indicating a power that allows appropriate measurement of the flow volume when the flow volume is relatively large (in other words, when a flow velocity is relatively high). On the other hand, if the comparison result is that the flow volume is less than or equal to the threshold value, the laser power target value setting device 32 may set, as the target value, a value indicating a power that is less than a present power of the laser light. Here, the "value indicating the power that is less than the present power" may include zero (i.e., the light source 12 is off).

(Control Process)

A process of controlling the irradiating device 10 by the controller 30 will be explained with reference to a flowchart in FIG. 2.

Figure 2:
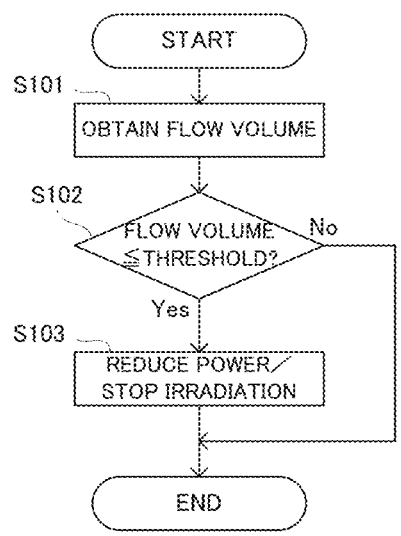
FIG. 2 is a flowchart illustrating a control process of an irradiating device according to the first practical example.

In FIG. 2, firstly, the controller 30 obtains the flow volume on the basis of the flow volume detection signal outputted from the flow volume detector 23 (step S101). The controller 30 then determines whether or not the flow volume is less than or equal to the threshold value (which corresponds to the comparison between the flow volume and the threshold value in the comparator 311 described above) (step S102).

In the determination in the step S102, if it is determined that the flow volume is greater than the threshold value (the step S102: No), the process illustrated in FIG. 2 is ended (in which case the irradiation of the laser light with the present power is continued). The controller 30 then performs the step S101 again after a lapse of a predetermined time. Therefore, the process illustrated in FIG. 2 is repeatedly performed in cycles corresponding to the predetermined time.

On the other hand, in the determination in the step S102, if it is determined that the flow volume is less than or equal to the threshold value (the step S102: Yes), the laser power target value setting device 32 of the controller 30 sets a new target value, and reduces the power of the laser light or stops the irradiation of the laser light (step S103). If the power of the laser light is reduced, or if the irradiation of the laser light is stopped, the controller 30 is desirably configured to inform a user of a reduction in the flow volume, for example, by giving a warning on an image display (not illustrated). By virtue of such a configuration, if a measurement target is a blood that flows in a tubing that constitutes an extracorporeal circulation blood circuit, such as, for example, an artificial dialyzer, it is possible to facilitate measures to restore the flow volume, system restart, or the like.

According to the laser Doppler blood-flowmetry 100 in the first practical example, if the flow volume of the blood of the test object is less than or equal to the threshold value, the power of the laser light is reduced, or the irradiation of the laser light is stopped. It is thus possible to prevent unexpectedly high energy from being applied to the blood of the test object, by the laser light, when the flow volume of the blood is reduced for some reasons. On the other hand, if the flow volume of the blood of the test object is greater than the threshold value, the laser light with a relatively strong power is applied. It is thus possible to appropriately measure the flow volume even if the flow volume of the blood is relatively large.

In the first practical example, the flow volume of the blood is obtained on the basis of the optical detection signal, but a flow velocity of the blood may be obtained, instead of or in addition to the flow volume. In this case, the laser power target value setting device 32 may set a target value in accordance with a result of a comparison between the flow velocity of the blood and a threshold value by the comparator 311.

The "photocurrent converter 21" according to the first practical example is an example of the "first light receiving device" according to the present invention. The "flow volume detector 23" according to the first practical example is an example of the "obtaining device" according to the present invention. The "controller 30" according to the first practical example is an example of the "controlling device" according to the present invention.

First Modified Example

The flow volume determinator 31 may be provided with a multi-stage comparator. In this case, by setting different threshold values inputted to the multi-stage comparator, it is possible to relatively flexibly set the power of the laser light in accordance with the flow volume of the blood.

Figure 3:
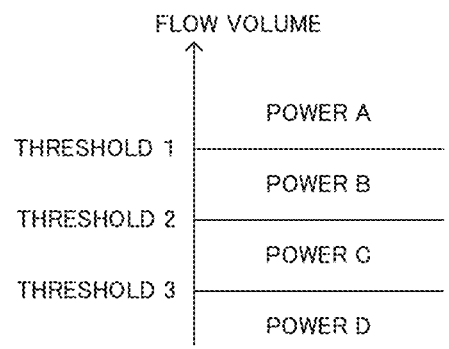
FIG. 3 is a diagram illustrating an example of a relation between a flow volume and a laser light power.

Alternatively, the laser power target value setting device 32 may be configured to have a function of the flow volume determinator 31 as well. In this case, for example, if a map for defining a relation between the flow volume and the power, as illustrated in FIG. 3, is stored in advance in a memory (not illustrated) of the laser power target value setting device 32, then, it is possible to relatively flexibly set the power of the laser light in accordance with the flow volume of the blood.

Second Modified Example

The flow volume detector 23 may be configured to obtain the flow volume of the blood from each of the average frequency and the first-order moment based on the optical detection signal. In this case, when the flow volume obtained from the first-order moment is less than a predetermined value, which is a specific example of the "second predetermined value" according to the present invention, the flow volume detector 23 may output a flow volume detection signal associated with the fluid information that indicates the flow volume obtained from the first-order moment. On the other hand, when the flow volume obtained from the first-order moment is greater than the predetermined value, the flow volume detector 23 may output a flow volume detection signal associated with the fluid information that indicates the flow volume obtained from the average frequency.

This is because the following experimental result has been obtained; namely, if the flow volume of the fluid is relatively large (i.e., the flow velocity is high), accuracy is higher when the average frequency is used to obtain the flow volume or the flow velocity than when the first-order moment is used, and if the flow volume of the fluid is relatively small (i.e., the flow velocity is low), the accuracy is higher when the first-order moment is used to obtain the flow volume or the flow velocity than when the average frequency is used.

Third Modified Example

In the aforementioned first practical example, if it is determined that the flow volume is less than or equal to the threshold value (the step S102: Yes), the laser power target value setting device 32 of the controller 30 sets a new target value, and reduces the power of the laser light or stops the irradiation of the laser light (the step S103). Instead of this, if it is determined that the flow volume is less than or equal to the threshold value, the controller may perform a control to intermittently emit the laser light.

Second Practical Example

Figure 4:
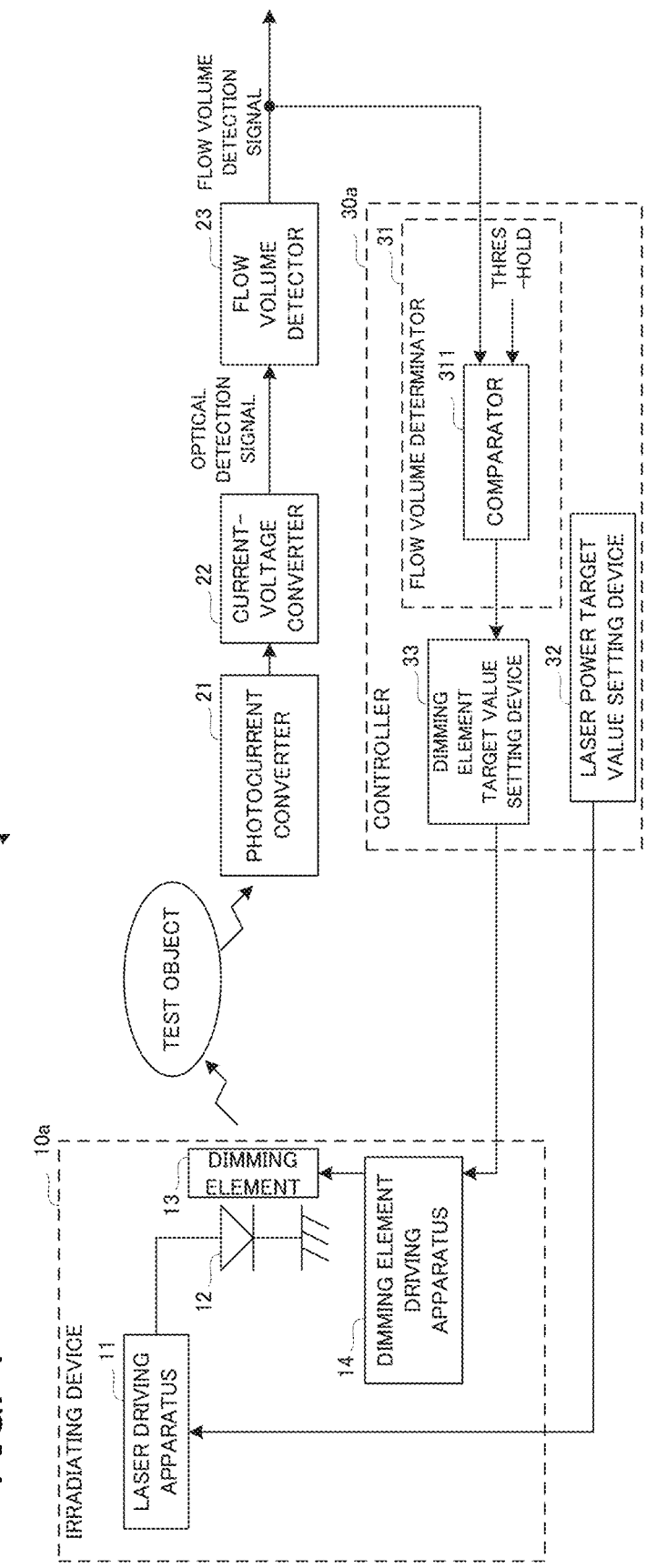
FIG. 4 is a block diagram illustrating a configuration of a laser Doppler blood-flowmetry according to a second practical example.

A laser Doppler blood-flowmetry according to a second practical example will be explained with reference to FIG. 4. The second practical example is the same as the first practical example, except that it is partially different in the configuration of the irradiating device and the controller. Thus, in the second practical example, an explanation of the same part as in the first practical example will be omitted, and the same parts on the drawings will carry the same referential numerals. Basically, only the different point will be explained with reference to FIG. 4. FIG. 4 is a block diagram illustrating a configuration of a laser Doppler blood-flowmetry according to the second practical example.

(Configuration)

In FIG. 4, an irradiating device 10a of a laser Doppler blood-flowmetry 200 is provided with a dimming element 13 configured to reduce laser light emitted from the light source 12, and a dimming element driving apparatus configured to drive the dimming element 13. Here, the expression "to reduce laser light" may conceptually include cutting off the laser light. To the dimming element 13, for example, a liquid crystal element (a liquid crystal shutter) and a mechanical shutter can be applied. A controller 30a is provided with a dimming element target setting device 33 configured to set a target value that indicates a degree of the reduction in the laser light by the dimming element 13.

The dimming element target setting device 33 is configured to set the target value associated with the dimming element 13 in accordance with the comparison result from the comparator 311. Specifically, if the comparison result is that the flow volume is greater than the threshold value, the dimming element target setting device 33 may set, as the target value, a value at which a present transmission amount (or amount of passing) of the laser light is maintained. On the other hand, if the comparison result is that the flow volume is less than or equal to the threshold value, the dimming element target setting device 33 may set, as the target value, a value indicating a transmission amount (or amount of passing) that is less than the present transmission amount (or amount of passing) of the laser light.

In the second practical example, the target value set by the laser power target value setting device 32 is typically constant; namely, the power of the laser light emitted from the light source 12 is typically constant.

According to the laser Doppler blood-flowmetry 200 in the second practical example, if the flow volume of the blood of the test object is less than or equal to the threshold value, the laser light emitted from the irradiating device 10a is reduced or cut off by the dimming element 13. It is thus possible to prevent unexpectedly high energy from being applied to the blood of the test object, by the laser light, when the flow volume of the blood is reduced for some reasons. On the other hand, if the flow volume of the blood of the test object is greater than the threshold value, the laser light with a relatively strong power is applied. It is thus possible to appropriately measure the flow volume even if the flow volume of the blood is relatively large.

The second practical example can also adopt the same configurations as those in the first and second modified examples associated with the first practical example described above.

Third Practical Example

Figure 5:
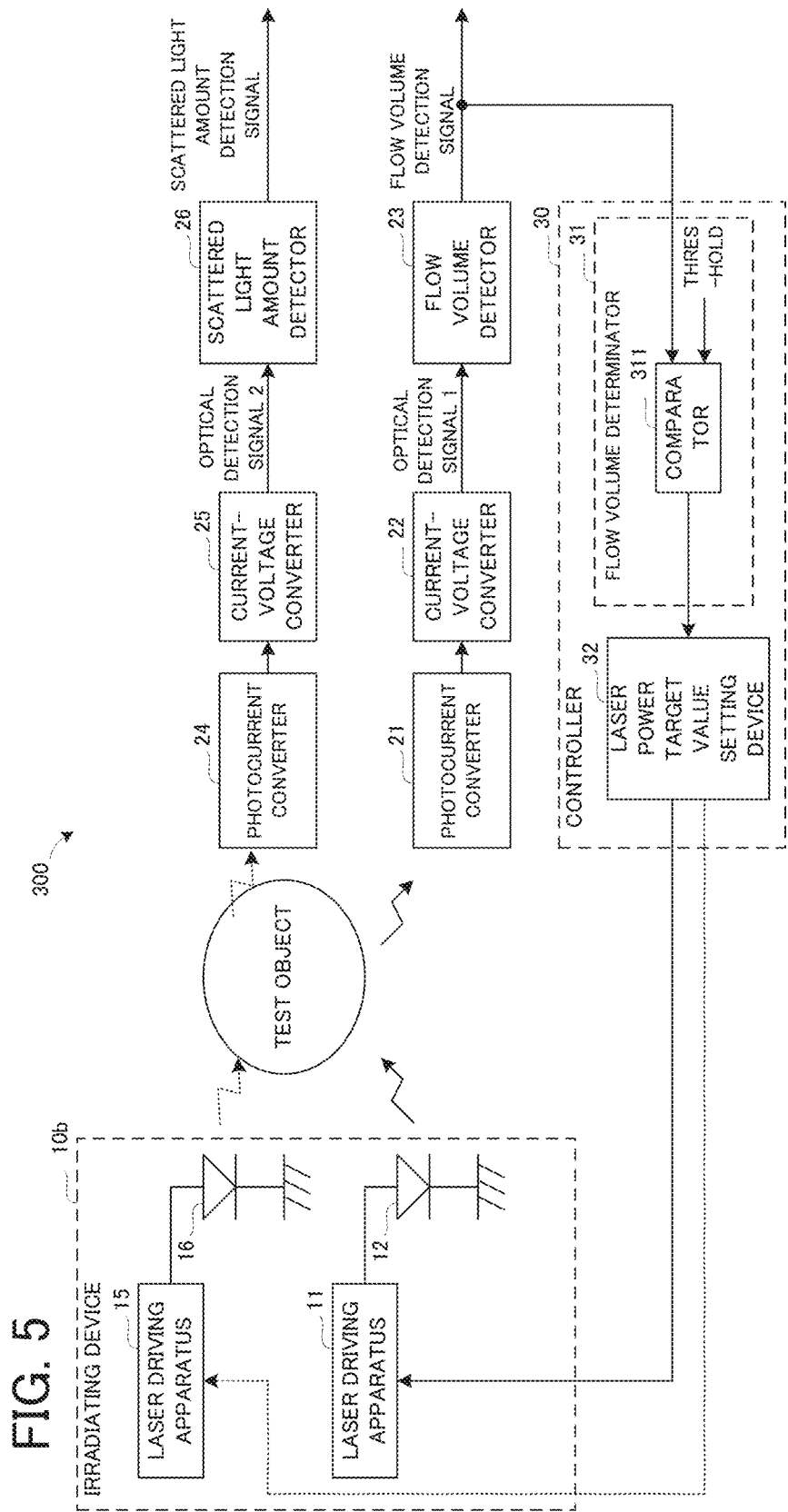
FIG. 5 is a block diagram illustrating a configuration of a laser Doppler blood-flowmetry according to a third practical example.

A laser Doppler blood-flowmetry according to a third practical example will be explained with reference to FIG. 5. The third practical example is the same as the first practical example, except that it is partially different in the configuration of the irradiating device, and except that a configuration of measuring the light amount of the laser light scattered by the test object is added. Thus, in the third practical example, an explanation of the same part as in the first practical example will be omitted, and the same parts on the drawings will carry the same referential numerals. Basically, only the different point will be explained with reference to FIG. 5. FIG. 5 is a block diagram illustrating a configuration of a laser Doppler blood-flowmetry according to the third practical example.

The laser light scattered by the test object may mean, for example, transmitted light including forward-scattered light, or reflected light including backscattered light, or the like.

(Configuration)

In FIG. 5, a laser Doppler blood-flowmetry 300 is provided with an irradiating device 10b, photocurrent converters 21 and 24, current-voltage converters 22 and 25, the flow volume detector 23, a scattered light amount detector 26, and the controller 30.

The irradiating device 10b is provided with a light source 12 configured to mainly emit laser light for measuring the flow volume of a blood, a laser driving apparatus 11 configured to drive the light source 12, a light source 16 configured to mainly emit laser light for measuring a transmittance of the blood, and a laser driving apparatus 15 configured to drive the light source 16.

The photocurrent converter 24 is configured to receive light including light scattered by the test object, out of the laser light emitted from the light source 16, and to output a current signal corresponding to a light amount of the received light. The current-voltage converter 25 is configured to convert the current signal outputted from the photocurrent converter 24, to a voltage signal, and to output it as an optical detection signal (refer to an "optical detection signal 2" in FIG. 5). The scattered light amount detector 26 is configured to output a scattered light amount detection signal, which indicates an amount of the light scattered by the blood (in other words, intensity of the scattered light), on the basis of the optical detection signal outputted from the current-voltage converter 25. A detailed explanation regarding how to obtain the scattered light amount on the basis of the optical detection signal will be omitted because the various existing methods can be applied.

The scattered light detection signal may be inputted, for example, to a not-illustrated concentration detector. The concentration detector may detect (or estimate) a blood concentration (e.g., a hematocrit value, etc.) from the scattered light detection.

If the comparison result is that the flow volume is greater than the threshold value, the laser power target value setting device 32 may set, as a target value associated with the laser driving apparatus 11, a value indicating a power that allows appropriate measurement of the flow volume when the flow volume is relatively large (in other words, when the flow velocity is relatively high). On the other hand, if the comparison result is that the flow volume is less than or equal to the threshold value, the laser power target value setting device 32 may set, as the target value associated with the laser driving apparatus 11, a value indicating a power that is less than a present power of the laser light.

The laser power target value setting device 32 is configured to maintain a target value associated with the laser driving apparatus 15, regardless of the comparison result of the comparator 311. Here, when the scattered light amount detection signal is used to measure the concentration of the blood, it is possible to accurately measure the concentration of the blood even if the power of the laser light emitted from the light source 16 is significantly weaker (e.g. by 1/10 times) than the power of the laser light emitted from the light source 12 to measure the flow volume or the flow velocity. Thus, in the laser Doppler blood-flowmetry 300, the power of the laser light emitted from the light source 16 is set to be significantly less than the power of the laser light emitted from the light source 12 if the flow volume is greater than the threshold value. It is therefore considered that there is no problem even if it is continued to irradiate the test object with the laser light emitted from the light source 16 when the flow volume is less than or equal to the threshold value.

According to the laser Doppler blood-flowmetry 300 in the third practical example, if the flow volume of the blood of the test object is less than or equal to the threshold value, the power of the laser light emitted from the light source 12 is reduced, or the irradiation of the laser light is stopped. It is thus possible to prevent unexpectedly high energy from being applied to the blood, which is the test object, by the laser light, when the flow volume of the blood is reduced for some reasons. On the other hand, if the flow volume of the blood of the test object is greater than the threshold value, the laser light with a relatively strong power is emitted from the light source 12 and is applied to the test object. It is thus possible to appropriately measure the flow volume even if the flow volume of the blood is relatively large.

Particularly in the third practical example, it is maintained to irradiate the test object with the laser light emitted from the light source 16, regardless of the flow volume of the blood. Thus, according to the laser Doppler blood-flowmetry 300, it is possible to change the power of the laser light emitted from the light source 12 in accordance with the flow volume of the blood, while maintaining the measurement of the transmittance of the blood.

The third practical example can also adopt the same configurations as those in the first and second modified examples associated with the first practical example described above.

The present invention is not limited to the aforementioned embodiments and examples, but various changes may be made, if desired, without departing from the essence or spirit of the invention which can be read from the claims and the entire specification. A measuring apparatus, a measuring method, a computer program and a recording medium that involve such changes is also intended to be within the technical scope of the present invention.

DESCRIPTION OF REFERENCE NUMERALS AND LETTERS 10, 10a, 10b irradiating device
11, 15 laser driving apparatus
12, 16 light source
13 dimming element
14 dimming element driving apparatus
21, 24 photocurrent converter
22, 25 current-voltage converter
23 flow volume detector
269 scattered light amount detector
30, 30a controller
31 flow volume determinator
32 laser power target value setting device
33 dimming element target value setting device
100, 200, 300 laser Doppler blood-flowmetry

The invention claimed is:
1. A measuring apparatus comprising:
a first irradiating device configured to apply light to a fluid;
a first light receiving device configured to receive light scattered by the fluid, out of the light applied by said first irradiating device, and configured to output a first output signal;

an obtaining device configured to obtain fluid information, which indicates a flow volume or a flow velocity of the fluid, on the basis of the first output signal of said first light receiving device; and a controlling device configured to control said first irradiating device, on the basis of the fluid information.

2. The measuring apparatus according to claim 1, wherein the first output signal includes a beat signal caused by a Doppler shift of the light, and said obtaining device is configured:

to obtain the fluid information on the basis of average frequency information and first-order moment information based on the beat signal;

to obtain the fluid information on the basis of the average frequency information if the flow volume or the flow velocity of the fluid indicated by the fluid information is greater than or equal to a second predetermined value; and to obtain the fluid information on the basis of the first-order moment information if the flow volume or the flow velocity of the fluid indicated by the fluid information is less than the second predetermined value.

3. The measuring apparatus according to claim 1, wherein said controlling device is configured to control said first irradiating device to reduce intensity of the light applied to the fluid, or to stop irradiation of the light applied to the fluid, if the flow volume or the flow velocity of the fluid indicated by the fluid information is less than or equal to a first predetermined value.

4. The measuring apparatus according to claim 3, further comprising:

a second irradiating device configured to apply light to the fluid; and a second light receiving device configured to receive light scattered by the fluid, out of the light applied by said second irradiating device, and configured to output a second output signal, wherein said controlling device is configured to control said first irradiating device to reduce the intensity of the light applied to the fluid from said first irradiating device, or to stop irradiation of the light applied to the fluid, while controlling said second irradiating device to maintain intensity of the light applied to the fluid from said second irradiating device, if the flow volume or the flow velocity of the fluid indicated by the fluid information is less than or equal to the first predetermined value.

5. The measuring apparatus according to claim 3, wherein said first irradiating device has a dimming device configured to reduce the light applied to the fluid, and said controlling device is configured to control said first irradiating device to reduce the intensity of the light applied to the fluid by using the dimming device, if the flow velocity of the fluid indicated by the fluid information is less than or equal to the first predetermined value.

6. The measuring apparatus according to claim 5, further comprising:

a second irradiating device configured to apply light to the fluid; and a second light receiving device configured to receive light scattered by the fluid, out of the light applied by said second irradiating device, and configured to output a second output signal, wherein said controlling device is configured to control said first irradiating device to reduce the intensity of the light applied to the fluid from said first irradiating device, or to stop irradiation of the light applied to the fluid, while controlling said second irradiating device to maintain intensity of the light applied to the fluid from said second irradiating device, if the flow volume or the flow velocity of the fluid indicated by the fluid information is less than or equal to the first predetermined value.

7. A measuring method in a measuring apparatus including: a first irradiating device configured to apply light to a fluid; and a first light receiving device configured to receive light scattered by the fluid, out of the light applied by the first irradiating device, and configured to output a first output signal, said measuring method comprising:

an obtaining process of obtaining fluid information, which indicates a flow volume or a flow velocity of the fluid, on the basis of the first output signal of the first light receiving device; and a controlling process of controlling the first irradiating device, on the basis of the fluid information.

8. A non-transitory computer readable medium recording a computer program for making a computer, which is provided in a measuring apparatus including: a first irradiating device configured to apply light to a fluid; and a first light receiving device configured to receive light scattered by the fluid, out of the light applied by the first irradiating device, and configured to output a first output signal, function as:

an obtaining device configured to obtain fluid information, which indicates a flow volume or a flow velocity of the fluid, on the basis of the first output signal of the first light receiving device; and a controlling device configured to control the first irradiating device, on the basis of the fluid information.

* * * * *